(12) United States Patent
Beach et al.

(10) Patent No.: US 10,152,823 B2
(45) Date of Patent: Dec. 11, 2018

(54) THREE-DIMENSIONAL IMAGE PROCESSING TO LOCATE NANOPARTICLES IN BIOLOGICAL AND NONBIOLOGICAL MEDIA

(71) Applicant: CYTOVIVA, INC., Auburn, AL (US)

(72) Inventors: James M. Beach, Auburn, AL (US); Samuel M. Lawrence, Auburn, AL (US); Byron J. Cheatham, Auburn, AL (US); James L. Uertz, Auburn, AL (US); Robert P. Dougherty, Bellevue, WA (US)

(73) Assignee: CYTOVIVA, INC., Auburn, AL (US)

( * ) Notice: Subject to any disclaimer, the term of this patent is extended or adjusted under 35 U.S.C. 154(b) by 33 days.

(21) Appl. No.: 14/775,309

(22) PCT Filed: Mar. 12, 2014

(86) PCT No.: PCT/US2014/024346
§ 371 (c)(1),
(2) Date: Sep. 11, 2015

(87) PCT Pub. No.: WO2014/165091
PCT Pub. Date: Oct. 9, 2014

(65) Prior Publication Data
US 2016/0027206 A1 Jan. 28, 2016

Related U.S. Application Data

(60) Provisional application No. 61/776,977, filed on Mar. 12, 2013.

(51) Int. Cl.
*G06K 9/00* (2006.01)
*G06T 17/00* (2006.01)
(Continued)

(52) U.S. Cl.
CPC ......... *G06T 17/00* (2013.01); *G01N 21/6458* (2013.01); *G02B 21/10* (2013.01);
(Continued)

(58) Field of Classification Search
None
See application file for complete search history.

(56) References Cited

U.S. PATENT DOCUMENTS 7,564,623 B2 * 7/2009 Vodyanoy .............. G02B 21/10
359/368
2002/0098588 A1 7/2002 Sammak et al.
(Continued)

FOREIGN PATENT DOCUMENTS

JP 2009223348 2/1995
JP 2002531840 9/2002
(Continued)

OTHER PUBLICATIONS

Wang et al., "Size-dependent endocytosis of gold nanoparticles studied by three-dimensional mapping of plasmonic scattering images", Journal of Nanobiotechnology, Dec. 20, 2010, pp. 1-13.*
(Continued)

*Primary Examiner* — Matthew Bella
*Assistant Examiner* — Jose M Torres
(74) *Attorney, Agent, or Firm* — Thomas Horstemeyer,LLP

(57) ABSTRACT

Disclosed are various embodiments for methods and systems for three-dimensional imaging of subject particles in media through use of dark-field microscopy. Some examples, among others, include a method for obtaining a three-dimensional (3D) volume image of a sample, a method for determining a 3D location of at least one subject particle within a sample, a method for determining at least one spatial correlation between a location of at least one subject
(Continued)

particle and a location of at least one cell structure within a cell and/or other similar biological or nonbiological structure, a method of displaying a location of at least one subject particle, method for increasing the dynamic range of a 3D image acquired from samples containing weak and strong sources of light, and method for sharpening a 3D image in a vertical direction.

19 Claims, 4 Drawing Sheets

(51) Int. Cl.
| | | |
|---|---|---|
| *G02B 21/10* | (2006.01) | |
| *G02B 21/36* | (2006.01) | |
| *G01N 21/64* | (2006.01) | |
| *G02B 21/16* | (2006.01) | |
| *G06T 5/00* | (2006.01) | |
| *G06T 7/00* | (2017.01) | |
| *G06T 15/08* | (2011.01) | |
| *G06T 15/50* | (2011.01) | |
| *G01N 15/00* | (2006.01) | |
| *G01N 15/14* | (2006.01) | |

(52) U.S. Cl.
CPC .......... *G02B 21/16* (2013.01); *G02B 21/367* (2013.01); *G06T 5/004* (2013.01); *G06T 7/0012* (2013.01); *G06T 15/08* (2013.01); *G06T 15/506* (2013.01); *G01N 2015/0038* (2013.01); *G01N 2015/1445* (2013.01); *G06T 2200/04* (2013.01); *G06T 2207/10056* (2013.01); *G06T 2207/30004* (2013.01); *G06T 2210/41* (2013.01)

(56) References Cited

U.S. PATENT DOCUMENTS

| | | | | |
|---|---|---|---|---|
| 2003/0228053 | A1* | 12/2003 | Li | G06T 7/55 382/154 |
| 2011/0254943 | A1* | 10/2011 | Ozinsky | G01N 21/6458 348/79 |
| 2012/0200694 | A1* | 8/2012 | Garsha | G01N 21/6456 348/79 |
| 2013/0129181 | A1* | 5/2013 | Glensbjerg | G01N 15/1475 382/133 |

FOREIGN PATENT DOCUMENTS

| | | |
|---|---|---|
| JP | 2004513481 A | 4/2004 |
| JP | 2007140322 A | 6/2007 |
| JP | 2011145191 A | 7/2011 |
| JP | 2013029836 | 2/2013 |
| JP | 2013507612 | 3/2013 |
| WO | 2011046807 A2 | 4/2011 |

OTHER PUBLICATIONS

Sarder et al., "Deconvolution methods for 3-D fluorescence microscopy", IEEE Signal Processing Magazine, vol. 23, Issue: 3, May 2006, pp. 32-45.*
International Search Report dated Sep. 24, 2014.
Wang Sheng-Hann et al "Size-dependent endocytosis of gold nanoparticles studied by three-dimensional mapping of plasmonic scattering images"; Journal of Nanobiotechnology, Biomed Central, GB., vol. 8, No. 1, Dec. 20, 2010 (Dec. 20, 2010), p. 33.
Sri Rama Prasanna Pavani et al "3D microscopy with a double-helix point spread function"; SPIE, P.O. Box 10 Bellingham WA 98227-0010 USA, vol. 7184, Sep. 3, 2009 (Sep. 3, 2009).
Sheng-Hann Wang,"Size-dependent endocytosis of gold nanoparticles studied by three-dimensional mapping of plasmonic scattering images",Journal of Nanobiotechnology,Dec. 20, 2010, vol. 8,pp. 1-13.
Japanese Patent Application 2016-501501 filed Mar. 12, 2014, Foreign Office Action dated Nov. 28, 2017.
CN Office Action for related Application No. 2014800252975, filed Mar. 12, 2014, dated May 16, 2017.
Response to Japanese Office Action filed Feb. 28, 2018 in Japaense Patent Application 2016-501501 f.
Response to Chinese Office Action filed May 16, 2018 in co-pending related Chinese Application No. 2014800252975.
Japanese Patent Application 2016-501501 filed Mar. 12, 2014, Foreign Office Action dated Jul. 24, 2018.
Shinya Ogikubo, Autofluorescent Lifetime Imaging: Detection of Intracellular pH in a Single Cell, [online], 2012 [retrieved on Jul. 5, 2018], URL, http://molsci.center.ims.ac.jp/area/2012/papers/4A17_m.pdf (for exemplifying a well-known art, newly cited).
Chinese Patent Application 2014800252975 filed Mar. 12, 2014, Foreign Office Action dated Sep. 3, 2018.

* cited by examiner

THREE-DIMENSIONAL IMAGE PROCESSING TO LOCATE NANOPARTICLES IN BIOLOGICAL AND NONBIOLOGICAL MEDIA

CROSS-REFERENCE TO RELATED APPLICATIONS

This application is the 35 U.S.C. § 371 national stage application of PCT Application No. PCT/US2014/024346, filed Mar. 12, 2014, which claims priority to and the benefit of, U.S. provisional application entitled "THREE-DIMENSIONAL IMAGE PROCESSING TO LOCATE NANOPARTICLES IN BIOLOGICAL AND NONBIOLOGICAL MEDIA" having Ser. No. 61/776,977, filed Mar. 12, 2013, both of which are incorporated by reference in their entirety.

BACKGROUND

The introduction of drugs and chemical agents into living cells has recently begun to utilize nano-scale objects of less than 100 nanometer dimensions and/or microscopic objects, herein known as the subject particle, in various configurations as carriers. For example, therapeutic drugs can be coated onto, or encased within, nano-sized particles such as gold and silver. The functionalized subject particle is then introduced into the body, where it is absorbed into tissues and ultimately taken up by cells. The ability to target just the cells that should receive the drug is enabled by functional coatings on the particles, which are recognized by the cell surface. Research into the process of cell uptake of subject particles, and the intracellular processing of the drug-particle, is important for development of the drug therapy process. The cell-subject particle interactions that are involved in uptake and distribution within cells are elucidated by many different types of studies using diverse techniques.

One of the most widely used tools is cell imaging by fluorescent microscopy. Conventional fluorescent microscopy does not allow the three dimensional volume of the cell to be viewed. A confocal fluorescence microscope is therefore used to image thin sections of the cell over a volume to view the cell structure in three dimensions. However these methods require introduction of fluorescent labels. The attachment of fluorophores to subject particles or cell structures can alter the intended function for drug delivery and significantly increases the difficulty of the cell preparation. Systems and methods that permit determination of the location of subject particles in three dimensions without altering the intended function for drug delivery are therefore of interest and have the potential to play an important role in increasing the understanding of nano-drug delivery, thus furthering the development of nanomedicine.

SUMMARY

The present disclosure provides wide-field microscopy methods that can determine the locations of subject particles within unstained and fluorescing cells or in semi-transparent nonbiological media and other media through which light can be transmitted, for example fiber matrices. The present disclosure provides novel methods for acquisition of image data from functionalized subject particles within unstained and fluorescent cell preparations. Also provided are methods for producing three dimensional cell-subject particle images using broadband illumination scattered from the cell volume, as opposed to current methods requiring fluorescent cells and particles. Such an image can be acquired with a dark-field illumination method and the use of image sectioning techniques rather than by conventional fluorescence methods using filter cubes designed for specific fluorophores. Nonlimiting examples of suitable systems and methods of illumination are taught in U.S. Pat. No. 7,564,623, "Microscope Illumination Device and Adapter Therefor," and U.S. Pat. No. 7,542,203, "Microscope Illumination Device and Adapter Therefor," both of which are incorporated by reference herein in their entirety.

In addition, the present disclosure also provides novel computational methods to perform three-dimensional deconvolution of dark-field image sections and thereby reveal locations of subject particles in relation to the cell structure. The new methods employ multiple point spread functions (PSF) to correct the image focus across a wide spectral range, as opposed to single PSFs that are designed for specific fluorophore wavelengths. The new PSFs can be designed to work with variable and fixed iris objectives used for dark-field microscopy. The new deconvolution methods automatically detect cell structure and subject particles in images through use of separate PSFs for each cell structure and type of subject particle of interest to optimize the three-dimensional image reconstruction. As an example, the subject particle may be reflective over a narrow range of wavelengths whereas the cell image is produced over a wide range of wavelengths or over a different range of wavelengths.

A unique feature of the deconvolution is the conversion of the three-dimensional image of all of the subject particles into spherical icons, which are located precisely at the subject particle coordinates in the three dimensional volume. A data set comprised of all of the subject particle positions results from this method, and with it a user can then examine a particular subject particle of interest by moving a microscope stage along three dimensions to examine the location of that subject particle. For example, a user can examine a particular subject particle though use of hyperspectral microscopy to evaluate spectral properties that report whether the drug is attached or detached from the particle.

The methods of the present disclosure are different and unique in that they are able to operate with standard research wide-field microscopes rather than confocal microscopes. The elimination of the need for fluorescent labeling reduces complexity of the functionalized subject particle, which in many cases can alter the function. The broad spectral range over which the three-dimensional image can be rendered allows the methods to be used with diverse subject particle configurations that can be observed anywhere in the visible to near infrared wavelength range. No state-of-the-art method(s) in the field of optical microscopy is/are known to exist that can automatically determine subject particle positions within cells.

BRIEF DESCRIPTION OF THE DRAWINGS

Many aspects of the present disclosure can be better understood with reference to the following drawings. The components in the drawings, including any drawings incorporated herein by reference, are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
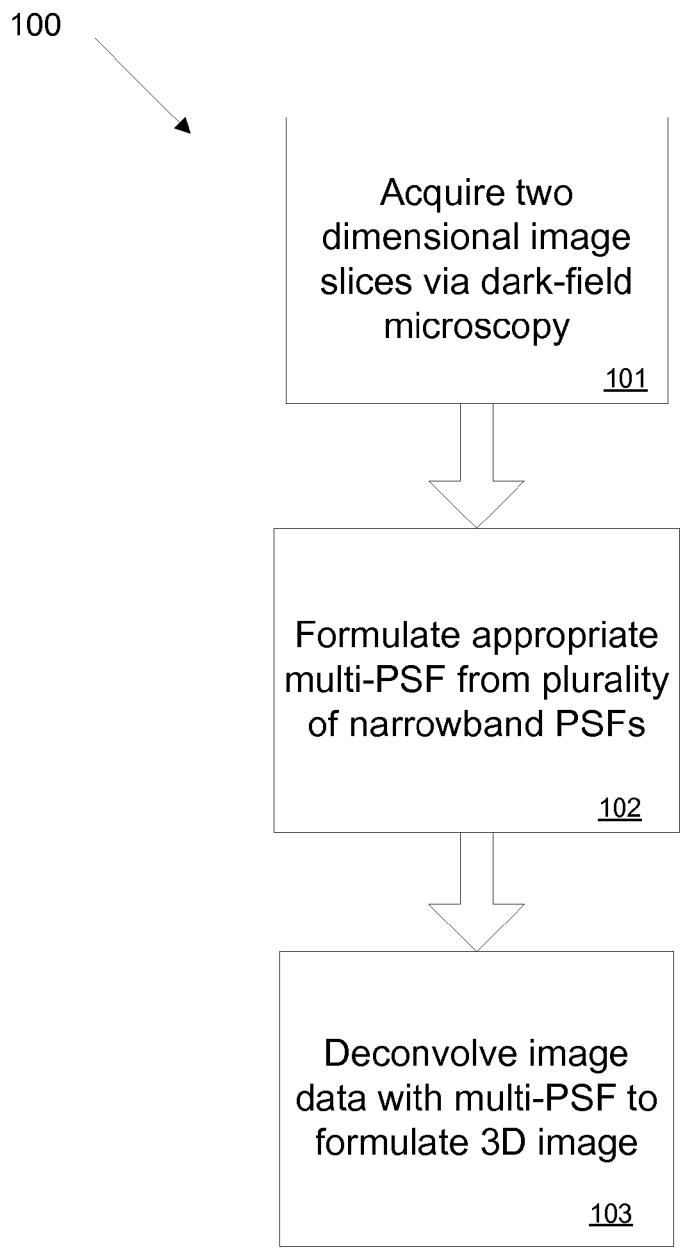
FIG. 1 is a flowchart illustrating a method of image formation according to various embodiments of the present disclosure.

In the following discussion, a general description of the system and its components is provided, followed by a discussion of the operation of the same. Herein are described embodiments of methods and systems for acquisition and computational processing of three-dimensional image data of subject particles in media through the use of dark-field microscopy. Objects that can be subject particles include functionalized metallic and non-metallic nanoparticles and nanorods, single and multi-walled carbon nanotubes, gold shells, quantum dots and nanofilaments. Although the illustrative embodiments discussed herein may refer to cellular media, the methods and systems of the present disclosure are not limited to biological media and can be used with any suitable transparent, semi-transparent, or translucent medium. Furthermore, although imaging of nanoparticles in cells represents one possible application of the methods and systems of the present disclosure, subject particles in the present disclosure need not be limited to nano-sized particles, but can be any size particles that can be imaged using the methods and systems of the present disclosure. Furthermore, media of the present disclosure need not be limited to biological materials such as cells, but can comprise such non-limiting examples as fiber matrices, filter matrices, emulsions, and any suitable transparent, semi-transparent, or translucent material that permits images to be obtained using the methods and systems of the present disclosure.

Referring now to the drawings, one or more preferred embodiments of the present disclosure are described.

Disclosed Methodologies

The methods and systems disclosed herein are directed to two general categories. Acquisition methods used to obtain three-dimensional (3D) image data of biological and non-biological media containing subject particles using dark-field microscopy are described. In addition, methods and systems are described that extend a 3D deconvolution process to image data not previously amenable to it.

Acquisition Methodologies

This section presents the methods and systems for acquisition 3D image data. A recording, using a dark-field imaging method, is made of a defined volume containing some media which can be interspersed with subject particles. The recording can be made in conjunction with any suitable dark-field microscopy system, such as, by way of non-limiting example, the system described in U.S. Pat. No. 7,564,623, "Microscope Illumination Device and Adapter Therefor." Media can be biological, such as cellular material, or nonbiological, such as a fiber matrix. Recordings of media without subject particles can also be obtained using the same technique. When subject particles are included, they do not need to be labeled fluorescently to be detected and localized with the process described in this disclosure. The media and cells can be supported by a glass slide and be stabilized under a cover slip, or they can be in an environmental flow chamber that can support live cells.

The recording consists of a stack of 2D images that are obtained with fixed distances in the vertical (or focus) direction between each image. In a live cell preparation, the cells and positions of subject particles should be stable in a temporal and spatial manner for the several seconds that are needed to acquire the stack of images. The image stack is recorded by alternately taking images and then moving the microscope stage to a new predetermined position along the vertical direction. The resulting image stack represents a low resolution representation of the volume, and is the input for the computational process. When both biological media and subject particles are unstained (non-fluorescent), the process allows for the use of broadband illumination which reflects indiscriminately from the cell and the subject particle. If the subject particle has a resonance peak at a specific wavelength, and the unstained cell has a different reflectance spectrum, the process allows for two spectra, one emphasizing the subject particle peak wavelength and the other characteristic of the cell reflectivity, the illumination, and the camera sensitivity, taken together. The method accounts for both spectra simultaneously, so that both types of objects are efficiently imaged.

Alternatively, the process allows the first narrowband wavelength to be shifted off the subject particle peak so that its contribution to the image is reduced. This second case is useful because the light reflecting from many of the subject particles used in cell studies is at least one magnitude stronger than the cell reflection. If highest efficiencies were used, the image would saturate at the locations of subject particles when the cell structure was at a reasonable value in the image. The present disclosure also describes a method for increasing the dynamic range of the recording of both types of objects using two recordings, each obtained with a high dynamic range camera, made at the same focus position, where the exposure time is set short in one image to capture the subject particles without saturation and made long in the other image to capture the cell structure. The process then replaces the saturated pixels in the long exposure image with the values of the same pixels in the short exposure image, where the values have been scaled to reflect a common exposure time and the data are now present in a floating point format. It is also possible to represent the new images in a fixed point format with more than 16 bits.

In some embodiments, the process also allows the cell structure to be fluorescently labeled. When the cell emission occurs at one wavelength, and the resonance peak of the subject particle is at a different wavelength, the computational process can take advantage of the separate wavelengths, as described below, by use of separate point spread functions for each. This type of acquisition can be performed with a continuum spectrum type of light source, such as a quartz halogen source.

When the cell fluorescence is instead excited by the strong peak of an arc lamp, such as a mercury arc, there is the additional advantage that the signal from the cell structure can be raised relative to the signal from unlabeled subject particles. To accomplish this, a controlled mixture of narrowband with a wideband light is needed, the first for the cell structure and the second for the subject particle, so that relative signal strength from each object can be adjusted. The Dual Mode Fluorescence Module developed and manufactured by Cytoviva is a non-limiting example of a device for the mixing of light from two spectral regions. The device contains a fluorescence excitation filter in a rotatable wheel that passes the narrowband wavelengths. The device allows the filter to be moved slightly to one side to allow a portion of the unfiltered light source to also pass into the illumination beam. When the purpose is to image fluorescent objects, a multi-pass emission filter is added to the microscope. The narrow band of wavelengths emitting from the object passes through one channel of the multi-pass emission filter. The direct light coming out of the Dual Mode Fluorescence Module passes through the other channels of the multi-pass filter and is used to image the unstained objects. In practice the direct light from the arc lamp which passes through the remaining emission filter bands is away from the peaks of the arc lamp spectrum, and thus by this method the subject particle is illuminated less strongly than the cell structure. Since the amount of mixing can be proportionately controlled, the signal strengths from labeled cell structure and unlabeled subject particles can be equalized before the data is input into the computational process of 3D deconvolution. This last process can materially improve the 3D deconvolution by eliminating saturated pixels in the input data while maintaining high pixel values for the cell structure.

Extensions to 3D Deconvolution for Imaging Biological/Nonbiological Media Containing Subject Particles Using Dark-Field Microscopy This section discusses systems and methods of 3D deconvolution processes for computation of 3D imagery from data acquired as discussed above. In dark-field microscopy light is scattered from a source by objects. The strength of the scattering, and thus the image of the object, is relatively bright against a dark background in the recording made by the camera. In fluorescence the light is emitted by a label of the object. The strength of the fluorescence emission is relatively weak and the recorded fluorescence is contained within a narrow band of wavelengths. As opposed to the low light conditions in fluorescence, the light scattered from objects is contained in a broader band of wavelengths and is usually much stronger than the fluorescence. In unstained biological media such as cells containing subject particles this means there may be weak signal objects (cells) and strong signal objects (subject particles) which must both be processed in the deconvolution algorithm.

Next the applicable steps to create the processed 3D image from dark-field microscopy data are described. As shown in the flowchart of FIG. 1, image stacks, obtained as described above, are obtained and then input to a 3D deconvolution and display process, here known as the computation. By this approach 3D images of subject particles in biological and nonbiological media, where both are unstained, is obtainable by dark-field microscopy. 3D deconvolution has been previously described as a method for deblurring (sharpening) the image of fluorescent objects that are contained in an image stack. The present disclosure applies the method for the same purpose with non-fluorescent materials that are imaged with dark-field illumination.

The difference between fluorescence and dark-field reflected light is that the light originates directly from the fluorescent object over a narrow band of wavelengths whereas in dark-field reflected light, the objects are observed by light that originates from a light source that covers a broad range of wavelengths. When a laser is used for fluorescence excitation there can be coherent interference in the illumination bathing the sample, whereas in dark-field reflection, the use of incoherent light produces a more homogeneous illumination of the sample. The direct fluorescence emission from an object and light reflected from objects will in general possess different optical properties such as coherency and state of polarization. Fluorescence will be emitted only where fluorescent label is present, whereas dark-field light reflections are obtained from all material surfaces, and as such, the point sources of light differ. In some embodiments, the addition of broadband light adds a capability to 3D deconvolution methods where narrowband or laser light is not required or available.

In order to perform 3D deconvolution with broadband light, a new method has been developed. As further shown in the flowchart of FIG. 1, a unique multiple-point spread function (multiple-PSF) designed for the full range of wavelengths contained by the broadband light can be created from a combination of narrowband PSFs, either computed or measured, that cover the range of broadband wavelengths. The weighted integral described herein can be achieved in practice by summing individual PSFs made at a plurality of wavelengths. Several discrete wavelengths are picked within the spectral range of the broadband light. The exact number may depend on how much the point spread function changes with wavelength. For each center wavelength of a PSF, the spacing between circular rings in the PSF changes. In some embodiments a spacing between center wavelengths of every 50 nm to 100 nm is used to create the set of PSFs, which gives a good tradeoff in speed and accuracy of the deconvolution. A point spread function (PSF) can be calculated or measured for each wavelength. The PSFs are then summed together to obtain a multiple-PSF to allow deconvolution of the images formed by the broad band of light. If the strength of the light changes at different wavelengths, the different PSFs are weighted by the strength of the light at the center wavelength of the PSF before summing.

As further shown in the flow chart of FIG. 1, the image data is then deconvolved with the multiple-PSF as described herein to obtain the locations of the subject particles and formulate a 3D image. The process to apply a multi-psf is to first determine subject particle locations using a threshold and the spline peak finder described elsewhere in this document. Using a predetermined radius, the voxels in the input, non-interpolated, grid are classified as subject particle voxels or non-subject particle voxels according to whether they are located within the classification radius of a subject particle. During the deconvolution algorithm, the subject particle PSF is applied to the subject particle voxels, and the non-subject particle PSF is applied to the non-subject particle voxels. This, of course, breaks the translation-invariant assumption underlying the FFT-based high speed deconvolution. This problem is addressed by performing two FFT convolutions at each iteration: one using the subject particle source reconstruction and the other applying the non-subject particle source distribution. The results of the two convolutions are summed to produce the model used for the update at each stage. The update is applied to the subject particle or non-subject particle source according to the voxel location. In some embodiments, images that are contained in a stack of images, taken through a volume of the sample, are first blurred (made less sharp) using a low pass filter. This step reduces noise for the next step. The process then finds the brightest points in each of the blurred images, which are estimates of the exact location of subject particles, as subject particles are generally assumed to produce the brightest and most point-like parts of the dark-field images. The process then assumes, in one embodiment, a cubic spline form for the light intensity along the Z axis (which is the direction of focus). The z-value at which the spline reaches its maximum is determined, and this is taken as an estimate of the z value of the subject particle. This z value is, in general, in between the z values of the input image slices. The x and y values of the subject particle location are determined as the location of the locally brightest pixel in the smoothed images. Cubic splines are also used, in a later stage in the processing, to interpolate the deconvolved cell results to an isotropic grid.

In some embodiments, a separate set of PSFs for each type of object, one being the biological/nonbiological media and the other the subject particle, are optimal for the process described in the present disclosure. Some embodiments use a method whereby the subject particles are processed with one PSF and the rest of the biological or nonbiological media in the recording with at least one other PSF. The rationale is that each component is at a different wavelength (or range of wavelengths) and also that the 3D deconvolution process can be done separately for nanomaterials and cells or other objects and then recombined.

In some embodiments a dark-field imaging method is used specifically to illuminate and excite fluorescence label in biological or nonbiological media. Use of a dark-field illumination method in the context of fluorescence imaging, while not common practice, has been shown to be effective herein. In some embodiments, 3D image deconvolution is applicable when the subject particles are coated with functional chemistry which in turn alters the optical reflection or resonance property of the subject particle. This is possible because the acquisition and computational methods described herein are adapted for wideband imaging.

In some embodiments, 3D images of subject particles in biological or other media, where both are unstained, is obtainable by dark field microscopy. In some embodiments, the methods and systems described herein may be applied to only stained biological and nonbiological media. Although 3D imaging of fluorescently stained cells is known, in some embodiments determining the locations of unstained subject particles with respect to specific cell structure in fluorescing biological media, which express the specific cell structure by the fluorescent label, is obtainable by dark-field microscopy.

Methods for determining spatial relationships between subject particles and biological or nonbiological structures are also disclosed herein. As illustrated in the flow chart of FIG. 2, in some embodiments, a vector description of the subject particles contained in the 3D image is determined, where the x, y, and z coordinates are assigned to specific volume sectors (cubes) of the image, and cell structures overlapping the specific volume sectors are also determined, so that a quantitative description of the subject particle distribution in relation to cell structure is revealed. Some embodiments broaden and simplify the definition of the spatial relationship to be a binary outcome where the subject particle is either inside or outside the cell, or the biological or nonbiological object of interest. Some embodiments sharpen the deconvolved 3D image in the vertical direction by applying a peak isolation step to the vertical cubic spline function for each transverse pixel. For each vertical cubic spline function, this step starts by identifying all local minima in the function. The function between one local minimum and the next is a peak. The center of mass of this peak is determined and the peak is replaced by a function consisting of all zeros except for a value equal to the integrated area of the peak placed at the center of mass.

In some embodiments, a density function of subject particles, or in other words the concentration of subject particles in different parts of the cell interior, can be determined. This method uses the idea of the 3D cell sector described above. In some embodiments, this methodology can also be applied to stained cells. Some embodiments use stained media, where the subject particle can be located in relation to one or more specific cell structures revealed by fluorescent antibody labels to these structures, where the structures define the intracellular and extracellular space (cell plasma membrane), or the structures define the space interior or exterior to intracellular organelles (lysosome, nucleus etc). In some embodiments, the density function (concentration of subject particles) can also be enclosed by an intracellular organelle as well as the cell boundary.

Some embodiments employ user interactive methods where a specific cell structure can be selected by a user viewing the 3D volume display image, and the shortest distance between individual subject particles and the cell structure can be determined, and where line segments representing the minimum distance vector can be added for visual effect when a particular subject particle is subsequently selected. All of the forgoing novel methods are applicable to the study of subject particle transport in biological media.

In some embodiments, the presence of subject particles within the 3D image can be artificially marked as an aid in visualizing the particles in the presence of biological or other structures. In some embodiments, the location of a subject particle is displayed with spherical objects, or icons, where the center of the icon is at the x, y and z coordinate of the original subject particle, as determined by 3D computations, and the color of the icon is easily distinguishable from color of cell structure in the 3D image. In some embodiments, the icon and cell structure are displayed by solid and semi-transparent colors respectively, to facilitate the viewing of the subject particle icons within cell structure as the 3D image is rotated.

Figure 3:
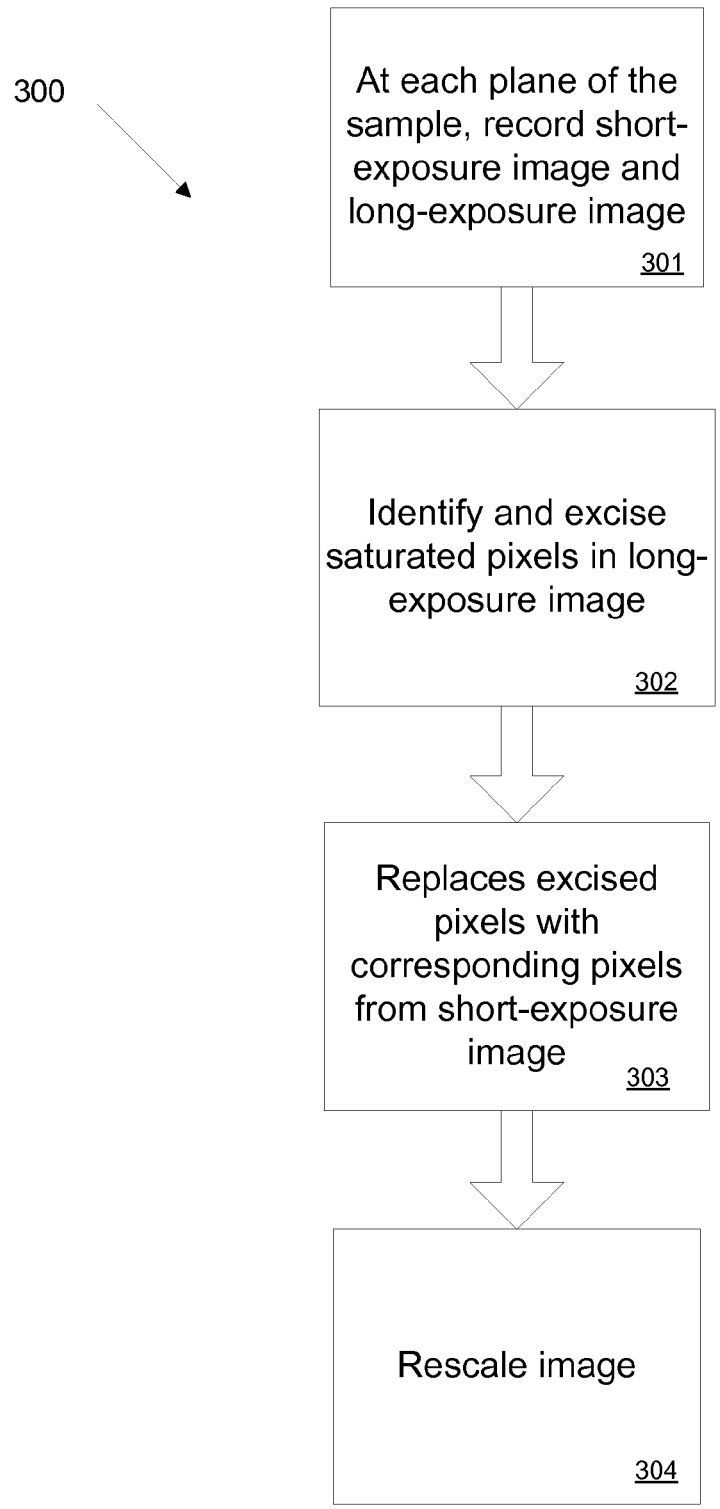
FIG. 3 is a flowchart illustrating a method of image formation according to various embodiments of the present disclosure.

As shown in the flowchart of FIG. 3, some embodiments comprise a method for acquisition and image computation which increases the range of values that can be contained in an image input into the full 3D deconvolution process, so that structure of the weaker signals from biological or other structures is faithfully rendered, while the significantly stronger signals that can come from subject particles is also kept within the full scale permitted for the image. By this method, at each plane of the sample, a set of images is recorded using different exposure times, one short and one long, where the short exposure captures the variation in light intensity of subject particles without causing image saturation, and where the long exposure captures the more subtle intensity variations caused by cell structure, and where a single image is created by identifying saturated pixels in the long exposure image and replacing their values with the values from identical pixels in the short exposure image, and rescaling the final image values to reflect a common exposure times.

Figure 4:
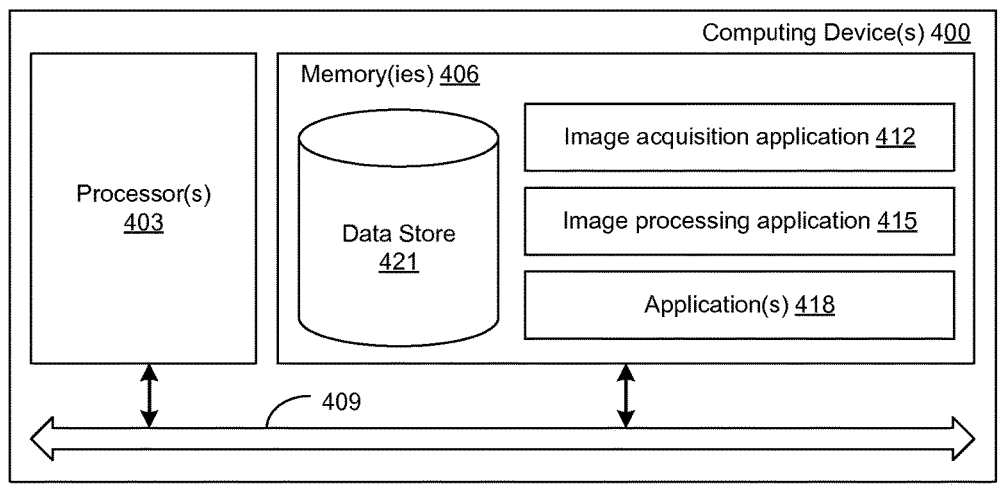
FIG. 4 is a schematic block diagram of a computing device according to various embodiments of the present disclosure.

With reference now to FIG. 4, shown is a schematic block diagram of a computing device 400 according to an embodiment of the present disclosure. The computing device 400 includes at least one processor circuit, for example, having a processor 403 and a memory 406, both of which are coupled to a local interface 409. To this end, the computing device 400 may comprise, for example, at least one server computer or like device. The local interface 409 may comprise, for example, a data bus with an accompanying address/control bus or other bus structure as can be appreciated.

Stored in the memory 406 are both data and several components that are executable by the processor 403. In particular, stored in the memory 406 and executable by the processor 403 are an image acquisition application 412, an image processing application 415, and potentially other applications 418. The image acquisition application 412 and/or the image processing application 415 can implement, when executed by the computing device 400, various aspects of the computational processing as described above with respect to the flowcharts of FIGS. 1-3. For example, the image acquisition application 412 can facilitate acquisition and/or storage of recordings of images and the image processing application 415 can facilitate processing of the images. In some implementations, the image acquisition application 412 and image processing application 415 may be combined in a single application. Also stored in the memory 406 may be a data store 421 including, e.g., recordings, images, video and other data. In addition, an operating system may be stored in the memory 406 and executable by the processor 403. It is understood that there may be other applications that are stored in the memory and are executable by the processor 403 as can be appreciated.

Where any component discussed herein is implemented in the form of software, any one of a number of programming languages may be employed such as, for example, C, C++, C#, Objective C, Java®, JavaScript, Perl, PHP, Visual Basic®, Python®, Ruby, Delphi®, Flash®, or other programming languages. A number of software components are stored in the memory and are executable by the processor 403. In this respect, the term "executable" means a program file that is in a form that can ultimately be run by the processor 403. Examples of executable programs may be, for example, a compiled program that can be translated into machine code in a format that can be loaded into a random access portion of the memory 406 and run by the processor 403, source code that may be expressed in proper format such as object code that is capable of being loaded into a random access portion of the memory 406 and executed by the processor 403, or source code that may be interpreted by another executable program to generate instructions in a random access portion of the memory 406 to be executed by the processor 403, etc. An executable program may be stored in any portion or component of the memory including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 406 is defined herein as including both volatile and nonvolatile memory and data storage components. Volatile components are those that do not retain data values upon loss of power. Nonvolatile components are those that retain data upon a loss of power. Thus, the memory 406 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 403 may represent multiple processors 403 and the memory 406 may represent multiple memories 406 that operate in parallel processing circuits, respectively. In such a case, the local interface 409 may be an appropriate network that facilitates communication between any two of the multiple processors 403, between any processor 403 and any of the memories 406, or between any two of the memories 406, etc. The processor 403 may be of electrical or of some other available construction.

Although portions of the image acquisition application 412, image processing application 415, and other various systems described herein may be embodied in software or code executed by general purpose hardware, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

The image acquisition application 412 and image processing application 415 can comprise program instructions to implement logical function(s) and/or operations of the system. The program instructions may be embodied in the form of source code that comprises human-readable statements written in a programming language or machine code that comprises numerical instructions recognizable by a suitable execution system such as a processor in a computer system or other system. The machine code may be converted from the source code, etc. If embodied in hardware, each block may represent a circuit or a number of interconnected circuits to implement the specified logical function(s).

Figure 2:
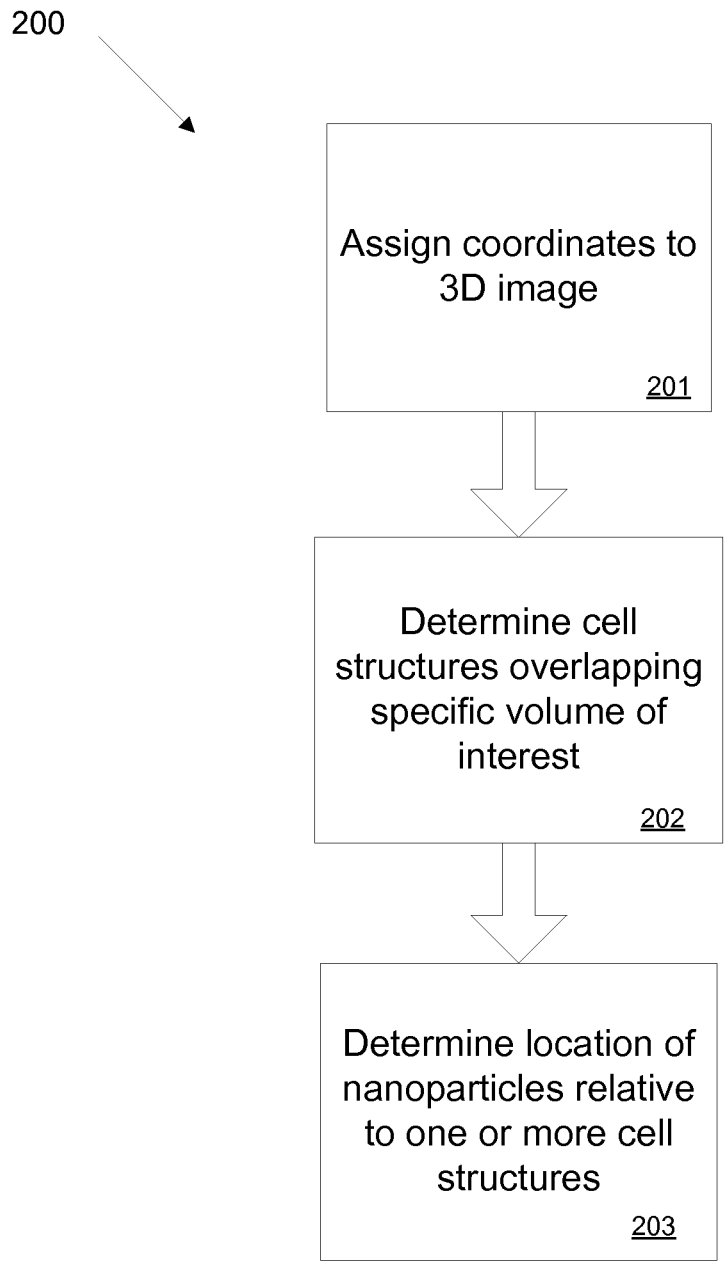
FIG. 2 is a flowchart illustrating a method of subject particle location according to various embodiments of the present disclosure.

Although the flowchart of FIGS. 1-3 show a specific order of execution, it is understood that the order of execution may differ from that which is depicted. For example, the order of execution of two or more blocks may be scrambled relative to the order shown. Also, two or more blocks shown in succession in FIGS. 1-3 may be executed concurrently or with partial concurrence. Further, in some embodiments, one or more of the blocks shown in FIGS. 1-3 may be skipped or omitted (in favor, e.g., measured travel times). In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the image acquisition application 412 and image processing application 415 that comprises software or code can be embodied in any non-transitory computer-readable medium for use by or in connection with an instruction execution system such as, for example, a processor 403 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

In an embodiment, among others, a method for obtaining a three-dimensional volume image of a sample is provided including obtaining, by dark-field microscopy, a plurality of two-dimensional images from the sample, the plurality of images comprising at least one two-dimensional image taken at each of a plurality of equally spaced sample locations along a direction of focus, each two-dimensional image containing both in-focus and out-of-focus light from the sample; inputting the plurality of two-dimensional images to a three-dimensional computational method for determining a location of at least one structure present in the sample; and formulating a three-dimensional volume image of the sample, the three-dimensional image showing the location of the at least one structure present in the sample.

In any one or more embodiments, the sample can comprise at least one cell and/or other similar biological or nonbiological structure; and at least one unstained subject particle within the at least one cell. The dark-field microscopy can use broadband light for illumination of the sample. The at least one cell and/or other similar biological or nonbiological structure can be fluorescent; the at least one unstained subject particle can be non-fluorescent; and/or the dark-field microscopy can comprise broadband light combined with specific wavelengths of fluorescence excitation light for illumination of the sample. The at least one structure present in the sample can comprise: at least one cell and/or other similar biological or nonbiological structure; at least one labeled cell structure within the at least one cell and/or other similar biological or nonbiological structure; and/or at least one non-fluorescent subject particle within the at least one cell and/or other similar biological or nonbiological structure. The dark-field microscopy can comprise a mixture of narrowband light and broadband light to illuminate the sample, the narrowband light exciting the at least one labeled cell structure and the wideband light scattering from the at least one non-fluorescent subject particle.

In any one or more embodiments, the method can comprise adjusting the relative strengths of the narrowband light and the wideband light to equalize the brightness of the at least one labeled cell structure and the at least one subject particle in the image, the at least one labeled cell structure contributing weakly and the at least one subject particle contributing strongly to the image and/or showing the location of at least one labeled cell structure and the location of the at least one subject particle in the three-dimensional image without saturation. In any one or more embodiments, the method can comprise generating the mixture of narrowband and wideband light through use of an arc lamp that contains at least one peak in its spectral output, light intensity of the arc lamp being strong over a narrow wavelength range defined by the at least one peak and weak over wide wavelength ranges outside the narrow wavelength range defined by the at least one peak; passing light from the arc lamp through an excitation filter with a pass band that passes the wavelength of the at least one peak; illuminating the at least one labeled cell structure with narrowband light passed through the excitation filter; illuminating the at least one subject particle simultaneously with broadband light from the arc lamp; receiving light through a first pass band of an emission filter, the first pass band passing light emitted from the at least one labeled cell structure and not light within the pass band of the excitation filter; and/or receiving light through a second pass band of the emission filter, the second pass band of the emission filter not passing light within the first pass band of the emission filter.

In another embodiment, a method for determining a three-dimensional (3D) location of at least one subject particle within a sample is provided including obtaining at least two images of the sample by dark-field microscopy, each of the two images being taken at a different sample location along a direction of focus; analyzing the at least two images via 3D deconvolution, wherein the analyzing comprises use of at least one multiple-point spread function (multiple-PSF); determining the location of the at least one subject particle from the result of the analyzing the at least two images via 3D convolution; and obtaining one or more 3D images, the one or more 3D images showing the 3D location of the at least one subject particle.

In any one or more embodiments, the dark-field microscopy can comprise broadband light. The at least one multiple-PSF can comprise a spectrally weighted integral of a plurality of narrowband PSFs over a wavelength range. The plurality of narrowband PSFs can comprise at least one computed narrowband PSF and/or at least one measured narrowband PSF.

In any one or more embodiments, the method can comprise blurring the at least one 3D image; interpolating the at least one 3D image in the direction of focus; and/or locating peaks within the at least one 3D image. The at least one multiple-PSF can comprise a subject particle voxel PSF and a separate non-subject particle voxel PSF. The at least one subject particle can be coated, the coating changing an optical spectrum of the at least one subject particle. The sample can be a biological sample. The biological sample can be unstained or stained. The sample can comprise semi-transparent material and/or a fiber matrix.

In another embodiment, a method for determining at least one spatial correlation between a location of at least one subject particle and a location of at least one cell structure within a cell and/or other similar biological or nonbiological structure is provided including determining the location of the at least one subject particle within a three-dimensional coordinate system; determining the location of the at least one cell structure within the three-dimensional coordinate system; formulating a vector description of the location of the at least one subject particle with respect to the location of the at least one cell structure in the three-dimensional coordinate system; and determining the spatial correlation from the vector description.

In any one or more embodiments, the method can comprise determining the location of the at least one subject particle with respect to a location of an intracellular space within the cell and/or other similar biological or nonbiological structure and/or determining the location of the at least one subject particle with respect to a location of an extracellular space outside the cell and/or other similar biological or nonbiological structure. In any one or more embodiments, the method can comprise obtaining a 3D density function enclosed by a boundary of the at least one cell structure, the 3D density function describing the plurality of subject particles. In any one or more embodiments, the method can comprise determining the location of the at least one subject particle with respect to a location of an intra-organelle space and/or determining the location of the at least one subject particle with respect to a location of an extra-organelle space.

In any one or more embodiments, the at least one subject particle comprises a plurality of subject particles. The at least one cell structure can comprise an organelle. The at least one cell structure can comprise the entire cell and/or other similar biological or nonbiological structure. The at least one cell structure can be stained or unstained. In any one or more embodiments, the method can comprise determining a minimum distance between the locations of the plurality of subject particles and the location of the at least one cell structure. The at least one cell structure can be a stained boundary of the cell and/or other similar biological or nonbiological structure. The at least one cell structure can be a stained nuclear membrane.

In another embodiment, a method of displaying a location of at least one subject particle is provided including obtaining at least two images of a sample by dark-field microscopy, each of the at least two images being taken at a different sample location along a direction of focus; analyzing the at least two images via 3D deconvolution, wherein the analyzing comprises use of at least one multiple-point spread function (multiple-PSF); determining the location of the at least one subject particle from the result of the analyzing the at least two images via 3D convolution; and obtaining one or more 3D images, the one or more 3D images showing the 3D location of the at least one subject particle by displaying a spherical icon at the 3D location of the at least one subject particle, the spherical icon representing a unique 3D spatial coordinate. In any one or more embodiments, the method can comprise displaying within the one or more 3D images a semi-transparent volume image of cell structure, the 3D location of the at least one subject particle being displayed inside the semi-transparent volume image of cell structure.

In another embodiment, a method for increasing the dynamic range of a three-dimensional image acquired from samples containing weak and strong sources of light is provided including obtaining, by dark-field microscopy, a short-exposure three-dimensional image from a sample, the short-exposure image being obtained through use a short exposure time; obtaining, by dark-field microscopy, a long-exposure three-dimensional image from the sample, the long-exposure image being obtained through use a long exposure time; identifying saturated pixels in the long-exposure image; excising the identified saturated pixels from the long-exposure image; replacing the excised pixels in the long-exposure image with corresponding pixels from the short-exposure image to form a final image; and rescaling the final image to reflect a common exposure time. In another embodiment, a method for sharpening a 3D image in a vertical direction is provided including processing a vertical profile of each transverse pixel to identify local minima and replacing portions of the profiles between the local minima with new profile portions that include zeros except for a single value equal to the integral of that portion, where the single value is located at the center of mass, in the vertical direction, of that portion.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, at least the following is claimed:

1. A method for obtaining a three-dimensional volume image of a sample, the method comprising:

obtaining, by dark-field microscopy, a plurality of two-dimensional images from the sample comprising subject particles and at least one cell, biological cellular material or tissue, nonbiological fiber matrix, filter matrix or emulsion, the plurality of two-dimensional images comprising at least one two-dimensional image taken at each of a plurality of equally spaced sample locations along a direction of focus, each two-dimensional image containing both in-focus and out-of-focus light from the sample, wherein:

the at least one cell, biological cellular material or tissue, nonbiological fiber matrix, filter matrix or emulsion is fluorescent;

the sample comprises at least one unstained subject particle within the at least one cell, biological cellular material or tissue, nonbiological fiber matrix, filter matrix or emulsion, where the at least one unstained subject particle is non-fluorescent; and the dark-field microscopy comprises broadband light combined with specific wavelengths of fluorescence excitation light for illumination of the sample over a narrow range of wavelengths;

inputting the plurality of two-dimensional images to a three-dimensional computational method for determining a location of the at least one cell, biological cellular material or tissue, nonbiological fiber matrix, filter matrix or emulsion present in the sample; and formulating a three-dimensional volume image of the sample, the three-dimensional volume image showing a location of the subject particles and the location of the at least one cell, biological cellular material or tissue, nonbiological fiber matrix, filter matrix or emulsion present in the sample.

2. The method of claim 1, wherein the broadband light provides continuum spectrum illumination of the sample over a wide range of wavelengths.

3. The method of claim 1, comprising:

analyzing the plurality of two-dimensional images via 3D deconvolution using at least one multiple-point spread function (multiple-PSF); and determining the location of the subject particles from a result of analyzing the plurality of two-dimensional images via 3D convolution.

4. The method of claim 1, wherein the broadband light combined with the specific wavelengths of fluorescence excitation light is generated through use of an arc lamp that contains at least one peak in its spectral output.

5. A method for obtaining a three-dimensional volume image of a sample, the method comprising:

obtaining, by dark-field microscopy, a plurality of two-dimensional images from the sample comprising subject particles and at least one cell, biological cellular material or tissue, nonbiological fiber matrix, filter matrix or emulsion, the plurality of two-dimensional images comprising at least one two-dimensional image taken at each of a plurality of equally spaced sample locations along a direction of focus, each two-dimensional image containing both in-focus and out-of-focus light from the sample, wherein the at least one cell, biological cellular material or tissue, nonbiological fiber matrix, filter matrix or emulsion present in the sample comprises:
at least one labeled cell structure within the at least one cell, biological cellular material or tissue, nonbiological fiber matrix, filter matrix or emulsion; and
at least one non-fluorescent subject particle within the at least one cell, biological cellular material or tissue, nonbiological fiber matrix, filter matrix or emulsion; and
the dark-field microscopy comprises a mixture of narrowband light in a narrow wavelength range and broadband light having a continuum spectrum of light in a wide wavelength range outside the narrow wavelength range to illuminate the sample, the narrowband light exciting the at least one labeled cell structure and the broadband light scattering from the at least one non-fluorescent subject particle;
inputting the plurality of two-dimensional images to a three-dimensional computational method for determining a location of the at least one cell, biological cellular material or tissue, nonbiological fiber matrix, filter matrix or emulsion present in the sample; and
formulating a three-dimensional volume image of the sample, the three-dimensional volume image showing a location of the subject particles and the location of the at least one cell, biological cellular material or tissue, nonbiological fiber matrix, filter matrix or emulsion present in the sample.

6. The method of claim 5, further comprising:
adjusting relative strengths of the narrowband light and the broadband light to equalize brightness of the at least one labeled cell structure and the at least one non-fluorescent subject particle in the three-dimensional volume image, the at least one labeled cell structure contributing weakly and the at least one non-fluorescent subject particle contributing strongly to the three-dimensional volume image; and
showing a location of at least one labeled cell structure and a location of the at least one non-fluorescent subject particle in the three-dimensional volume image without saturation.

7. The method of claim 5, further comprising:
generating the mixture of narrowband and broadband light through use of an arc lamp that contains at least one peak in its spectral output, light intensity of the arc lamp being strong over a narrow wavelength range defined by the at least one peak and weak over wide wavelength ranges outside the narrow wavelength range defined by the at least one peak;
passing light from the arc lamp through an excitation filter with a pass band that passes a wavelength of the at least one peak to produce the narrowband light;
illuminating the at least one labeled cell structure with the narrowband light passed through the excitation filter;
illuminating the at least one subject particle simultaneously with the broadband light from the arc lamp;
receiving light through a first pass band of an emission filter, the first pass band passing light emitted from the at least one labeled cell structure and not light within the pass band of the excitation filter; and
receiving light through a second pass band of the emission filter, the second pass band of the emission filter not passing light within the first pass band of the emission filter.

8. The method of claim 5, comprising:
analyzing the plurality of two-dimensional images via 3D deconvolution using at least one multiple-point spread function (multiple-PSF); and
determining the location of the subject particles from a result of analyzing the plurality of two-dimensional images via 3D convolution.

9. The method of claim 5, where in the mixture of narrowband and broadband light is generated through use of an arc lamp that contains at least one peak in its spectral output.

10. A method for obtaining a three-dimensional volume image of a sample, the method comprising:
obtaining, by dark-field microscopy, a plurality of two-dimensional images from the sample comprising subject particles and at least one cell, biological cellular material or tissue, nonbiological fiber matrix, filter matrix or emulsion, the plurality of two-dimensional images comprising at least one two-dimensional image taken at each of a plurality of equally spaced sample locations along a direction of focus, each two-dimensional image containing both in-focus and out-of-focus light from the sample;
inputting the plurality of two-dimensional images to a three-dimensional computational method for determining a location of the at least one cell, biological cellular material or tissue, nonbiological fiber matrix, filter matrix or emulsion present in the sample;
analyzing the plurality of two-dimensional images via 3D deconvolution using at least one multiple-point spread function (multiple-PSF);
determining a location of the subject particles from a result of analyzing the plurality of two-dimensional images via 3D convolution; and
formulating a three-dimensional volume image of the sample, the three-dimensional volume image showing the location of the subject particles and the location of the at least one cell, biological cellular material or tissue, nonbiological fiber matrix, filter matrix or emulsion present in the sample.

11. The method of claim 10, wherein the dark-field microscopy uses broadband light providing continuum spectrum illumination of the sample over a wide range of wavelengths.

12. The method of claim 10, wherein the dark-field microscopy comprises a mixture of narrowband light in a narrow wavelength range and broadband light having a continuum spectrum of light in a wide wavelength range outside the narrow wavelength range to illuminate the sample.

13. The method of claim 12, comprising adjusting relative strengths of the narrowband light and the broadband light to equalize brightness of at least one labeled cell structure and the at least one cell, biological cellular material or tissue, nonbiological fiber matrix, filter matrix or emulsion and at least one of the subject particles in the three-dimensional volume image.

14. The method of claim 13, wherein the at least one cell, biological cellular material or tissue, nonbiological fiber matrix, filter matrix or emulsion comprises the at least one labeled cell structure; and
at least one non-fluorescent subject particle within the at least one cell, biological cellular material or tissue, nonbiological fiber matrix, filter matrix or emulsion.

15. The method of claim 12, wherein the mixture of narrowband and broadband light is generated through use of an arc lamp that contains at least one peak in its spectral output.

16. The method of claim 12, further comprising:
generating the mixture of narrowband and broadband light through use of an arc lamp that contains at least one peak in its spectral output, light intensity of the arc lamp being strong over a narrow wavelength range defined by the at least one peak and weak over wide wavelength ranges outside the narrow wavelength range defined by the at least one peak;
passing light from the arc lamp through an excitation filter with a pass band that passes a wavelength of the at least one peak to produce the narrowband light;
illuminating at least one labeled cell structure with the narrowband light passed through the excitation filter;
illuminating at least one subject particle simultaneously with the broadband light from the arc lamp;
receiving light through a first pass band of an emission filter, the first pass band passing light emitted from the at least one labeled cell structure and not light within the pass band of the excitation filter; and
receiving light through a second pass band of the emission filter, the second pass band of the emission filter not passing light within the first pass band of the emission filter.

17. The method of claim 10, wherein the sample further comprises at least one unstained subject particle within the at least one cell, biological cellular material or tissue, nonbiological fiber matrix, filter matrix or emulsion.

18. The method of claim 17, wherein the at least one cell, biological cellular material or tissue, nonbiological fiber matrix, filter matrix or emulsion is fluorescent, and the at least one unstained subject particle is non-fluorescent.

19. The method of claim 17, wherein the at least one cell, biological cellular material or tissue, nonbiological fiber matrix, filter matrix or emulsion comprises at least one labeled cell structure; and the at least one unstained subject particle is non-fluorescent.

* * * * *